United States Patent [19]
Alliger et al.

[11] Patent Number: 5,443,456
[45] Date of Patent: Aug. 22, 1995

[54] CATHETER WITH COLLAPSIBLE WIRE GUIDE

[75] Inventors: Howard M. Alliger, Melville; Joseph Librizzi, Huntington, both of N.Y.; Robert Ginsburg, Greenwood Village, Colo.

[73] Assignee: Misonix, Inc., Farmingdale, N.Y.

[21] Appl. No.: 195,915

[22] Filed: Feb. 10, 1994

Related U.S. Application Data

[62] Division of Ser. No. 9,207, Jan. 22, 1993, Pat. No. 5,306,261.

[51] Int. Cl.⁶ .......................................... A61M 25/00
[52] U.S. Cl. ................................ 604/280; 128/657; 128/772
[58] Field of Search ............... 604/95, 164, 264, 270, 604/280; 128/658, 772; 606/194

[56] References Cited

U.S. PATENT DOCUMENTS

| | | | |
|---|---|---|---|
| 3,777,761 | 12/1973 | Sheridan | 604/175 |
| 4,114,618 | 9/1978 | Vargas . | |
| 4,236,521 | 12/1980 | Lauterjung | 604/270 |
| 4,722,724 | 2/1988 | Schocket | 604/8 |
| 4,748,982 | 6/1988 | Horzewski et al. . | |
| 4,762,519 | 8/1988 | Frimberger | 604/270 |
| 4,794,931 | 1/1989 | Yock . | |
| 4,824,435 | 4/1989 | Giesy et al. | 604/280 |
| 4,850,358 | 7/1989 | Millar | 128/675 |
| 4,887,606 | 12/1989 | Yock et al. . | |
| 4,920,954 | 5/1990 | Alliger et al. . | |
| 5,000,185 | 3/1991 | Yock . | |
| 5,003,990 | 4/1991 | Osypka . | |
| 5,037,387 | 8/1991 | Quinn et al. | 604/270 |
| 5,040,548 | 8/1991 | Yock . | |
| 5,061,267 | 10/1991 | Zeiher | 606/194 |
| 5,061,273 | 10/1991 | Yock . | |
| 5,102,403 | 4/1992 | Alt | 128/772 |
| 5,112,310 | 5/1992 | Grobe | 604/175 |
| 5,131,407 | 7/1992 | Ischinger et al. | 128/657 |
| 5,342,300 | 8/1994 | Stefanadis et al. | 604/95 |

FOREIGN PATENT DOCUMENTS

| | | | |
|---|---|---|---|
| 0376692 | 8/1907 | France | 604/264 |
| 2934628 | 3/1981 | Germany | 604/270 |

*Primary Examiner*—C. Fred Rosenbaum
*Assistant Examiner*—N. Kent Gring
*Attorney, Agent, or Firm*—R. Neil Sudol; Henry D. Coleman

[57] ABSTRACT

A catheterization assembly comprises an elongate substantially cylindrical catheter having an outer surface, and a flexible collapsible guide element attached to the outer surface of the catheter at a distal end thereof. A guidewire extends generally parallel to the catheter and through the guide element so that the guide element is held in an extended guide configuration away from the outer surface.

4 Claims, 3 Drawing Sheets

CATHETER WITH COLLAPSIBLE WIRE GUIDE

This application is a division of application Ser. No. 08/009,207 filed Jan. 22, 1993 (now U.S. Pat. No. 5,306,261).

BACKGROUND OF THE INVENTION

This invention relates to a catheter. More particularly, this invention relates to a catheter with a wire guide for receiving a guidewire for aiding in a catheterization process. This invention also relates to a catheterization assembly.

Balloon angioplasty catheters and most atherectomy instruments, such as cutting and scraping devices, require over-the-wire guide systems. The guidewire directs the distal, working end of the catheter around bends in a blood vessel and serves in positioning the catheter tip into or through an appropriate area of an occlusion. This guidewire method minimizes injury, dissection and perforation of the blood vessel wall.

In currently used guidewire systems, there is usually both an extra lumen in the catheter through which the guidewire slides, stiffening the catheter, as well as a bend in the guidewire as it enters the catheter body, increasing the sliding friction between the catheter and the guidewire. See, for example, U.S. Pat. No. 5,061,273 to Yock and U.S. Pat. No. 4,748,982 to Horzewski et al.

In conventional guided catheters, the guidewire enters the catheter through the sidewall and at the distal end of the catheter. In such an assembly, the bending of the guidewire at the entrance hole, as the catheter slides over the wire, has a tendency to pull the end of the guidewire out of an artery or vascular side branch. This pulling occurs frequently, for example, where a guidewire cannot be placed too deeply into a coronary artery.

A further disadvantage of this conventional catheter guiding technique, if there is no separate lumen, is that a hole formed in the catheter sidewall for the passage of the guidewire leaks liquid from the side of the catheter rather than from the distal end where the liquid may be required for X-ray imaging, bathing the catheter tip, or clearing the field of blood. It is also possible that if the guidewire enters the catheter near its distal end, the bent guidewire will tend to tilt the catheter tip so that its aim is off center.

Particularly in coronary work and peripheral procedures below the knee, it would be highly desirable to minimize the number of lumens in the catheter, thereby increasing the flexibility of the catheter. In addition, particularly in such procedures, it would be advantageous to avoid sharp bends in the guidewire, thereby reducing friction between the guidewire and the catheter when the catheter is being moved to an occlusion. It would also be desirable to maintain the guidewire in a coaxial relationship with respect to the blood vessel right up to a blood clot.

OBJECTS OF THE INVENTION

An object of the present invention is to provide an improved catheter guidewire system.

Another object of the present invention is to provide a wire-guided catheter with relatively enhanced flexibility.

A more particular object of the present invention is to provide a wire-guided catheter wherein the number of lumens in the catheter is minimized.

A further object of the present invention is to provide a catheter assembly which has reduced friction between the guidewire and the catheter when the catheter is being moved to an occulsion.

Another particular object of the present invention is to provide a catheter assembly wherein sharp bends in the guidewire are avoided.

An additional object of the present invention is to provide a wire-guided catheter wherein leakage of liquid from the catheter lumen occurs only at the distal end of the catheter and not along the sidewall thereof.

Yet another particular object of the present invention is to provide a wire-guided catheter assembly wherein catheter steering is facilitated, for at least some applications.

These and other objects of the present invention will be apparent from the drawings and detailed descriptions herein.

SUMMARY OF THE INVENTION

A catheterization assembly comprises, in accordance with the present invention, an elongate substantially cylindrical catheter having an outer surface, and a flexible collapsible guide element attached to the outer surface of the catheter at a distal end thereof. A guidewire extends generally parallel to the catheter and through the guide element so that the guide element is held in an extended guide configuration away from the outer surface.

According to another feature of the present invention, the guide element is one of a plurality of flexible guide elements spaced from one another longitudinally along the catheter. In this embodiment of the invention, the guide elements may have different effective lengths, whereby the guidewire passes at a varying distance from the outer surface. On the one hand, where a relatively distal guide element has a longer effective length than a relatively proximal guide element, the guidewire diverges from the catheter at the distal end thereof. On the other hand, where a relatively distal guide element has a shorter effective length than a relatively proximal guide element, the guidewire converges towards the catheter at the distal end thereof.

The latter configuration, with a convergence of the guidewire and the catheter, enables a positioning of the distal tip of the guidewire in front of, but spaced from, the distal working end of the catheter. In the former configuration, where the guidewire is angled away from the catheter at the distal end thereof, the guidewire may be pointed at a natural bend in an artery or around a urinary stone, for instance, where the catheterization is of a urethra.

Pursuant to one specific embodiment of the present invention, the flexible guide element is a thread-like loop attached to the catheter. In a more particular embodiment of the invention, the loop is provided along its length, for example, at an acme or crest position, with a smaller, ancillary loop for receiving the guidewire. The ancillary loop is contained within or circumscribed by the larger main loop.

Pursuant to an alternative embodiment of the present invention, the flexible guide element is a flap-like appendage on the catheter. In this event, the flap-like guide element may be formed with an inherent spring bias tending to hold the guide element in a collapsed configuration against the outer surface of the catheter.

A flexible collapsible wire guide on a catheter in accordance with the present invention serves to minimize the number of catheter lumens, thereby enhancing catheter flexibility. Flexibility is desirable for facilitating the threading of a catheter through labyrinthine vascular passages, for example. Moreover, the flexible wire guide collapses against or next to the outer surface of the catheter when the guidewire is withdrawn, thereby avoiding injury to the vascular wall when the catheter is moved back and forth and minimizing the catheter diameter and further facilitating threading operations. Likewise, the collapsing wire guides will not interfere with the critical adjustment of the catheter.

In contrast to conventional guidewire attachment techniques, the instant invention avoids bending the guidewire, thereby reducing friction which otherwise arises when moving the catheter tip to an occlusion. In further contrast to such conventional guidewire attachment techniques, a catheterization assembly in accordance with the present invention can maintain the guidewire in a coaxial relationship with respect to a blood vessel, right up to a blood clot or through a partial lumen formed by an occlusion.

A catheter comprises, in accordance with another general embodiment of the present invention, an elongate substantially cylindrical catheter sidewall surrounding a lumen and having an outer surface defined by a given diameter. A guide projection is provided on the outer surface of the catheter sidewall at a distal end thereof. The guide projection extends in a radial direction beyond the sidewall outer surface and is provided with a bore extending substantially parallel to the catheter lumen.

Pursuant to another feature of the present invention, the projection takes the form of a round bump on the outer surface of the catheter sidewall.

Pursuant to an additional feature of the present invention, the projection is provided with at least one slit oriented substantially transversely to the lumen and the bore, thereby facilitating a bending of catheter in a region about the projection.

In all wire-guided catheter assemblies in accordance with the present invention, the guidewire is threaded down the outside of the catheter and therefore does not interfere with the distal, working end of the device.

It is to be noted that a wire-guided catheter in accordance with the present invention may be used for applications other than vascular, for example, in urinary tract catheterization.

Figure 1:
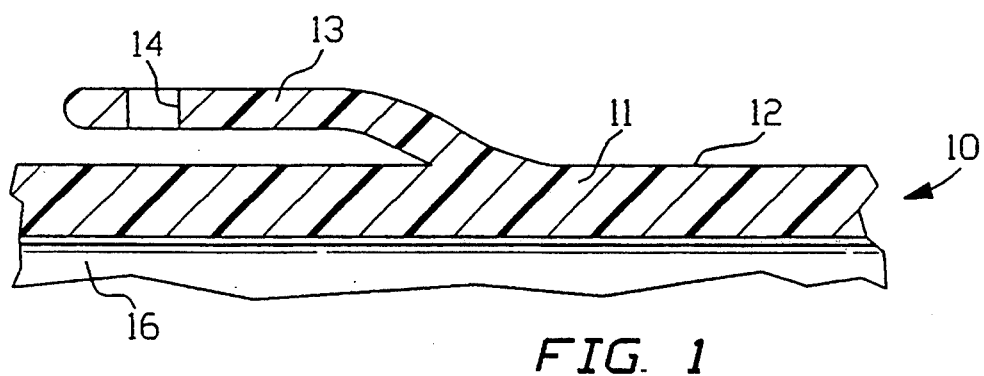
FIG. 1 is a partial longitudinal cross-sectional view, on an enlarged scale of a catheter with a flexible collapsible wire guide, in accordance with the present invention, showing the wire guide in a collapsed or neutral configuration.

In the drawings, the catheters are shown with the proximal ends to the left and the distal ends to the right.

DETAILED DESCRIPTION

Figure 2:
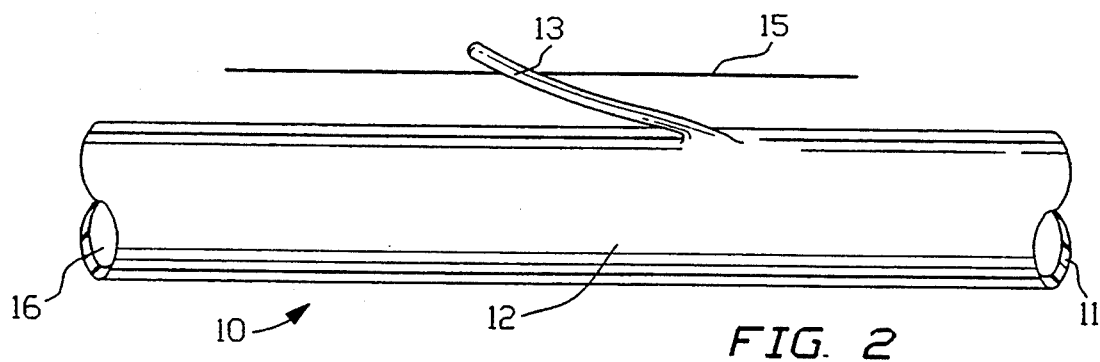
FIG. 2 is a partial side elevational view, on an enlarged scale, of the catheter of FIG. 1, showing insertion of a guidewire through the flexible guide.

As illustrated in FIGS. 1 and 2, a catheterization assembly includes an elongate substantially cylindrical catheter 10 having a sidewall 11 with a cylindrical outer surface 12. A flexible collapsible guide flap or wing 13 is attached to outer surface 12 of catheter 10 at or about a distal end thereof. Guide flap 13 is provided near a free end with an aperture 14 for receiving a guidewire 15, as depicted in FIG. 2.

As shown in FIG. 1, prior to the insertion of guidewire 15 (FIG. 2) and subsequently to the withdrawal thereof, guide flap 13 lies against and substantially parallel to catheter sidewall 11 and a cylindrical lumen 16 defined by the sidewall. Upon insertion of guidewire 15 (from a proximal end thereof) through aperture 14, guidewire 15 extends substantially parallel to catheter 10 and lumen 16, as depicted in FIG. 2. The passage of guidewire 15 through aperture 14 pulls guide flap 13 into an extended guide configuration away from sidewall surface 12, in a direction transverse to catheter 10.

Figure 3:
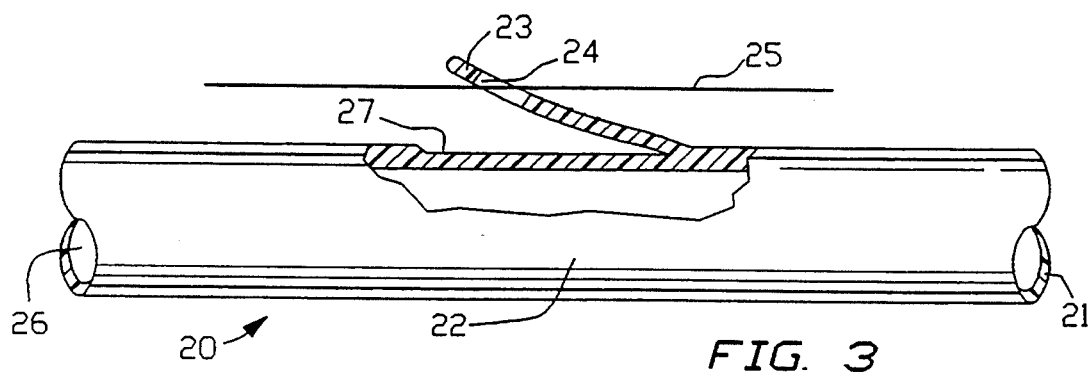
FIG. 3 is a partial side elevational view, partially in cross-section and on an enlarged scale, of another catheter with a flexible collapsible wire guide, in accordance with the present invention.

FIG. 3 illustrates a catheterization assembly similar to that of FIGS. 1 and 2. An elongate substantially cylindrical catheter 20 having a sidewall 21 with a cylindrical outer surface 22. A flexible collapsible guide flap or wing 23 is attached to outer surface 22 of catheter 20 at or about a distal end thereof. Guide flap 23 is provided near a free end with an aperture 24 for receiving a guidewire 25.

Prior to the insertion of guidewire 25 and subsequently to the withdrawal thereof, guide flap 23 lies against catheter sidewall 21 in a recess 27 in sidewall 21. Guide flap 23 may be formed by carving the flap out of sidewall 21 to form recess 27.

Catheter 20 has a cylindrical lumen 26 defined by sidewall 21. Upon insertion of guidewire 25 (from a proximal end thereof) through aperture 24, guidewire 25 extends substantially parallel to catheter 20 and holds guide flap 23 in an extended guide configuration away from sidewall surface 22.

Guide flaps 13 and 23 are typically approximately 1 mm thick and approximately 3 mm long.

Figure 4:
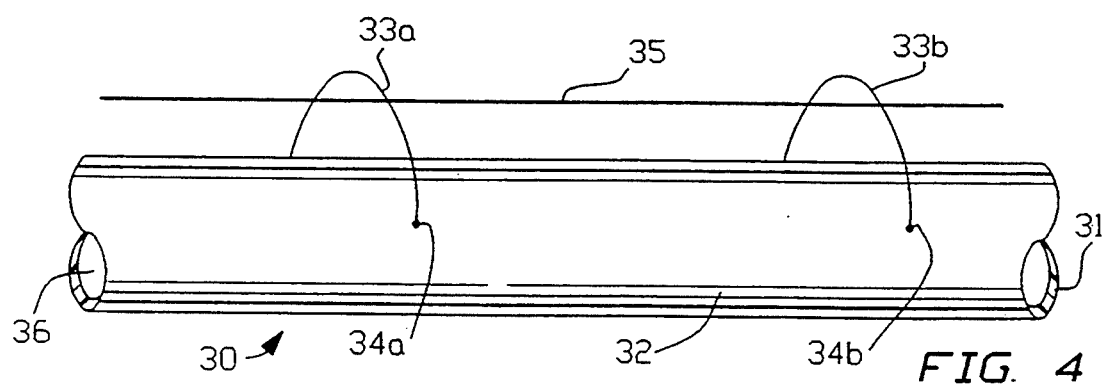
FIG. 4 is a partial side elevational view, on an enlarged scale, of a further catheter with a flexible collapsible wire guide, in accordance with the present invention.

As depicted in FIG. 4, another catheterization assembly includes an elongate substantially cylindrical catheter 30 having a sidewall 31 with a Cylindrical outer surface 32. A pair of flexible collapsible guide loops 33a and 33b are attached to outer surface 32 of catheter 30 at or about a distal end thereof. Guide loops 33a and 33b are attached at joints or weld points 34a and 34b to catheter sidewall 31 and receive a guidewire 35. Prior to the insertion of guidewire 35 and subsequently to the withdrawal thereof, guide loops 33a and 33b are foldable or collapsible against and catheter sidewall 31.

Upon insertion of guidewire 35 (from a proximal end thereof) through loops 33a and 33b, guidewire 35 extends substantially parallel to catheter 30 and a catheter lumen 36. The passage of guidewire 35 through loops 33a and 33b matinain the loops 33a and 33b in an extended guide configuration away from sidewall surface 32, in a direction transverse to catheter 30, as shown in FIG. 4.

Figure 5:
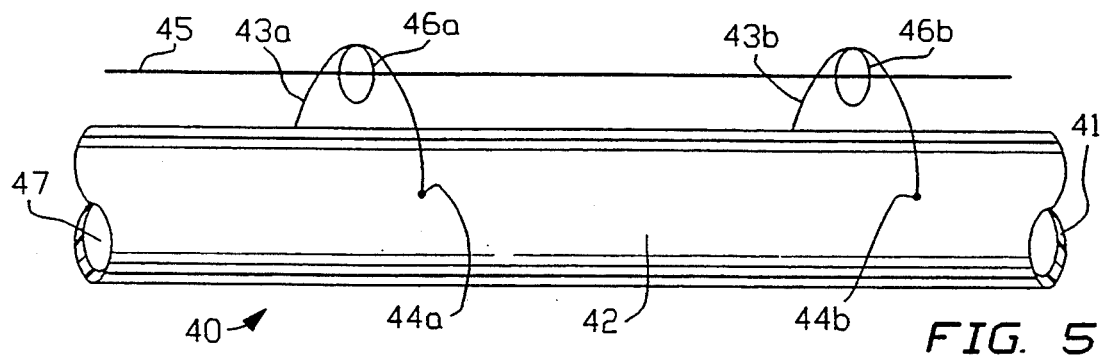
FIG. 5 is a partial side elevational view, on an enlarged scale, of a catheter with a modified flexible collapsible wire guide similar to that shown in FIG. 4.

FIG. 5 shows a modified embodiment of the catheterization assebmly of FIG. 4. As depicted in FIG. 5, an elongate substantially cylindrical catheter 40 has a sidewall 41 with a cylindrical outer surface 42. A pair of flexible collapsible guide loops 43a and 43b are attached to outer surface 42 of catheter 40 at or about a distal end thereof. Guide loops 43a and 43b are attached at joints or weld points 44a and 44b to catheter sidewall 41 and receive a guidewire 45. Prior to the insertion of guidewire 45 and subsequently to the withdrawal thereof, guide loops 43a and 43b are foldable or collapsible against and catheter sidewall 41.

Guide loops 43a and 43b are provided with smaller ancillary loops 46a and 46b attached to loops 43a and 43b at or about acmes or crests thereof, at points spaced farthest from catheter surface 42.

Upon insertion of guidewire 45 (from a proximal end thereof) through loops 46a and 46b, guidewire 45 extends substantially parallel to catheter 40 and a catheter lumen 47. The passage of guidewire 45 through loops 46a and 46b keep the main loops 43a and 43b in an extended guide configuration away from sidewall surface 42, in a direction transverse to catheter 40, as shown in FIG. 4.

Figure 6:
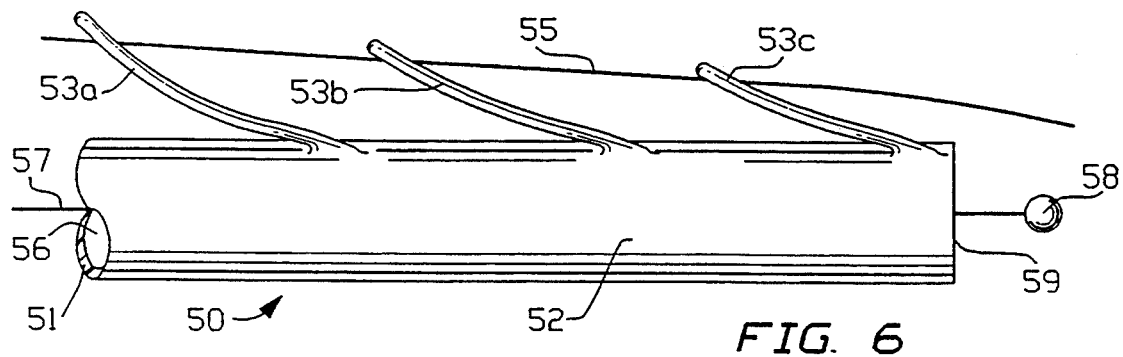
FIG. 6 is a side elevational view, on an enlarged scale, of the distal end of a catheter with an ultrasonic waveguide and with a plurality of flexible collapsible guidewire guides, in accordance with the present invention.

As illustrated in FIG. 6, a catheter 50 with a sidewall 51 having a cylindrical outer surface 52 is provided proximate to a distal tip 59 with a plurality of flap-like wire guides 53a, 53b, 53c which are flexible, collapsible, and perforated for receiving a guidewire 55. An ultrasonic waveguide wire 57 extends coaxially through a lumen 56 of catheter 50 and is formed at a distal end with a ball 58 for causing cavitation upon transmission of an ultrasonic axial wave through waveguide wire 57.

Flap-like wire guides 53a, 53b, and 53c have monotonically decreasing effective lengths: the closer a flap-like guide 53a, 53b, or 53c is to distal tip 59 of catheter 50, the closer to surface 52 is the respective perforation (not shown) traversed by wire 55. As depicted in FIG. 6, wire 55 accordingly converges towards catheter 50 at the distal end thereof. This convergence of guidewire 55 and catheter 50 enables a positioning of the distal tip of the guidewire in front of, but spaced from, cavitation ball 58 at the distal working end of catheter 50.

Figure 7:
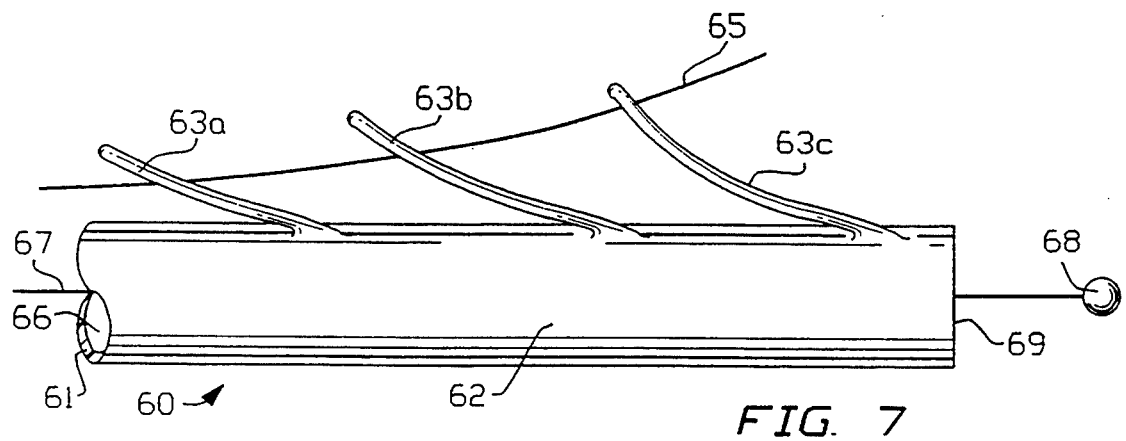
FIG. 7 is a side elevational view, on an enlarged scale, of the distal end of another catheter with an ultrasonic waveguide and with a plurality of flexible collapsible guidewire guides, in accordance with the present invention.

FIG. 7 shows a catheterization assembly similar to catheterization assembly of FIG. 6. A catheter 60 with a sidewall 61 having a cylindrical outer surface 62 is provided proximate to a distal tip 69 with a plurality of flap-like wire guides 63a, 63b, 63c which are flexible, collapsible, and perforated for receiving a guidewire 65. An ultrasonic waveguide wire 67 extends coaxially through a lumen 66 of catheter 60 and is formed at a distal end with a ball 68 for causing cavitation upon transmission of an ultrasonic axial wave through waveguide wire 67.

The middle flap-like wire guide 63b has effective length which is greater than the effective length of the more proximal guide 63a and less than the effective length of the more distal wire guide 63c. This change in effective guide length may be implemented by varying the distance of guide perforations (not shown) from catheter surface 62. As depicted in FIG. 7, wire 65 diverges from catheter 60 at the distal end thereof. This divergence of guidewire 65 and catheter 60 enables the guidewire 65 to be pointed at a natural bend in an artery or around a urinary stone, for instance, where the catheterization is of a urethra.

Figure 8:
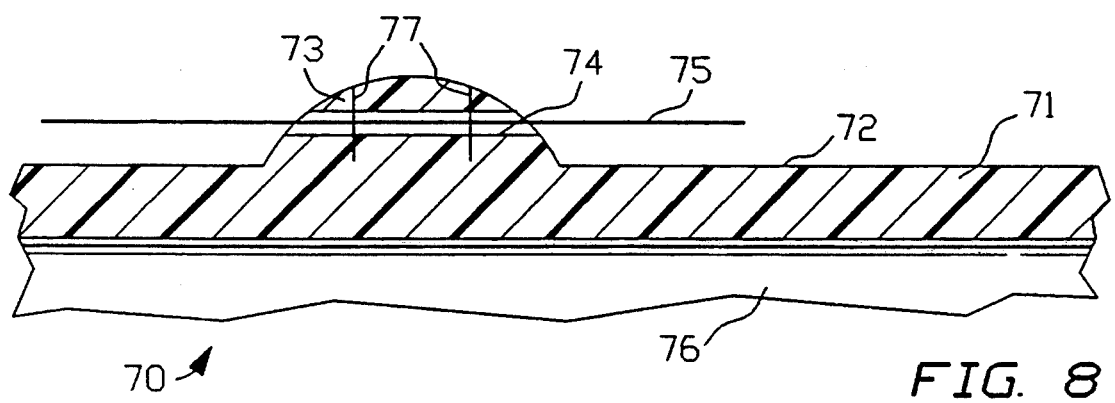
FIG. 8 is a partial longitudinal cross-sectional view, on an enlarged scale, of a catheter with a wire guide projection, in accordance with the present invention, showing the catheter in a straightened configuration.
Figure 9:
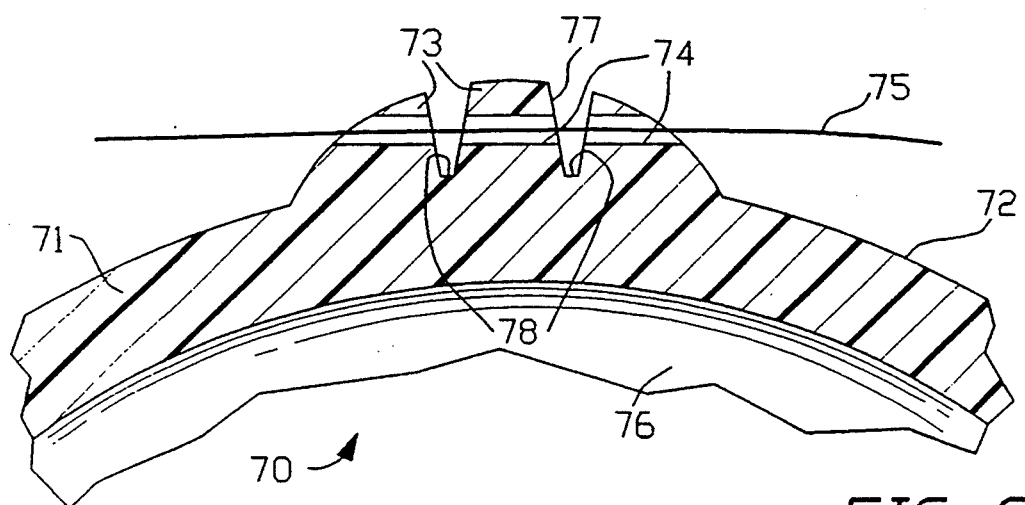
FIG. 9 is a partial longitudinal cross-sectional view, similar to FIG. 8, showing the catheter of FIG. 8 in a bent or arcuate configuration.

As illustrated in FIGS. 8 and 9, a catheter 70 with an elongate catheter sidewall 71 and a substantially cylindrical outer surface 72 surrounds a lumen 76. A projection 73 for guiding a guidewire 75 is provided on outer surface 72 of catheter sidewall 71 at a distal end thereof. Guide projection 73 extends in a radial direction beyond sidewall outer surface 72 and is provided with a bore 74 extending substantially parallel to catheter lumen 76. Projection 73 takes the form of a round bump on outer surface 72 of catheter sidewall 71. Projection 73 is provided with one or more slits 77 oriented substantially transversely to lumen 76 and bore 74, thereby facilitating a bending of catheter 70 in a region about projection 73, as depicted in FIG. 9.

It is to be noted that slits 77 may have a natural width as indicated by bottom surface 78 in FIG. 9. This width permits a bending of catheter 70 in a direction opposite to that illustrated in FIG. 9.

The projection type guidewire guide 73 of FIGS. 8 and 9 is utilizable particularly where the guidewire 75 is thin, for example, less that 0.030 inch ($\frac{3}{4}$ mm) and where the subject artery is not too small, for example, not less that 3 mm in internal diameter. Bump- or bullet-shaped guides 73 are then no more that 0.040 inch high. Slits 77 may be formed by a slicing operation.

In all of the catheters described herein, the guidewire guides are thin, both in a radial and an axial direction. The guidewires are maintained outside of the respective catheters, at least along distal end portions thereof, so that there are no sharp bends in the guidewires which would tend to pull the end of the guidewires out of an artery or vascular side branch and which increase friction between the guidewires and the catheters.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A catheter comprising:
    an elongate substantially cylindrical catheter wall having an outer surface, said catheter wall having a distal tip; and
    flexible guide means attached to said outer surface of said wall at a distal end thereof for flexing between a neutral configuration relatively collapsed against said outer surface and a guide configuration extending laterally outwardly from said outer surface and for slidably attaching, while in said guide configuration, a guidewire to said catheter wall, said flexible guide means including a thread-like loop attached to said wall, said thread-like loop being substantially spaced from said distal tip so that said thread-like loop can assume said neutral configuration, relatively collapsed against said outer surface.

2. The catheter defined in claim 1 wherein said loop is provided along its length with a smaller, ancillary loop for receiving said guidewire.

3. A catheterization assembly comprising:
an elongate substantially cylindrical catheter having an outer surface and a distal tip;
a flexible collapsible guide element in the form of a a thread-like loop attached to said outer surface of said catheter at a distal end thereof, said thread-like loop being substantially spaced from said distal tip so that said thread-like loop can alternately assume a neutral configuration relatively collapsed against said outer surface and a guide configuration extending laterally outwardly from said outer surface; and
a guidewire extending generally parallel to said catheter and through said guide element so that said guide element is held in said guide configuration, extended laterally away from said outer surface.

4. The catherization assembly defined in claim 3 wherein said loop is provided along its length with a smaller, ancillary loop for receiving said guidewire.

* * * * *